US005624976A

United States Patent [19]
Klee

[11] Patent Number: 5,624,976
[45] Date of Patent: Apr. 29, 1997

[54] DENTAL FILLING COMPOSITION AND METHOD

[75] Inventor: Joachim E. Klee, Radolfzell, Germany

[73] Assignee: Dentsply GmbH, Dreieich, Germany

[21] Appl. No.: 217,998

[22] Filed: Mar. 25, 1994

[51] Int. Cl.$^6$ .............................. A61K 6/087; C08K 3/22; C08L 63/02
[52] U.S. Cl. .................... 523/116; 523/414; 523/417; 524/431; 524/417; 524/436; 524/408; 433/228.1
[58] Field of Search .................................. 523/414, 417, 523/116, 117; 524/431, 417, 436, 408; 433/228.1

[56] References Cited

U.S. PATENT DOCUMENTS

| | | | |
|---|---|---|---|
| 3,066,112 | 11/1962 | Bowen | 260/41 |
| 3,256,226 | 6/1966 | Fekete et al. | 260/23.5 |
| 3,317,469 | 5/1967 | Feichtinger et al. | 260/47 |
| 3,327,016 | 6/1967 | Lee | 260/830 |
| 3,673,558 | 6/1972 | Toepel et al. | 260/29.2 |
| 3,709,866 | 1/1973 | Waller | 260/27 |
| 3,882,187 | 5/1975 | Takiyama et al. | 260/835 |
| 3,973,972 | 8/1976 | Muller | 523/116 |
| 3,980,483 | 9/1976 | Nishikubo et al. | 96/115 |
| 4,081,492 | 3/1978 | Traenckner et al. | 260/837 |
| 4,097,569 | 6/1978 | Waters | 264/255 |
| 4,097,994 | 7/1978 | Renville et al. | 525/922 |
| 4,100,045 | 7/1978 | Bogan et al. | 204/159.16 |
| 4,177,563 | 12/1979 | Schmite-Josten et al. | 523/116 |
| 4,182,833 | 1/1980 | Hicks | 523/417 |
| 4,197,390 | 4/1980 | Jackson | 528/115 |
| 4,229,376 | 10/1980 | Rogier | 260/563 |
| 4,255,468 | 3/1981 | Olson | 523/414 |
| 4,296,004 | 10/1981 | Rogier | 260/18 |
| 4,308,085 | 12/1981 | Horhold et al. | 156/330 |
| 4,383,879 | 5/1983 | Le Du et al. | 156/307.7 |
| 4,405,766 | 9/1983 | Bertram et al. | 525/507 |
| 4,524,161 | 6/1985 | Feuerhahn | 523/414 |
| 4,579,904 | 4/1986 | Orlowski et al. | 524/554 |
| 4,714,571 | 12/1987 | Schornick et al. | 528/103 |
| 4,758,643 | 7/1988 | Tannaka et al. | 526/279 |
| 4,806,381 | 2/1989 | Engelbrecht et al. | 427/2 |
| 4,816,495 | 3/1989 | Blackwell et al. | 522/14 |
| 4,931,096 | 6/1990 | Fujisawa et al. | 106/35 |
| 4,950,697 | 8/1990 | Chang et al. | 523/116 |
| 4,985,516 | 1/1991 | Sakashita et al. | 526/196 |
| 5,189,077 | 2/1993 | Kerby | 523/116 |
| 5,236,362 | 8/1993 | Cohen et al. | 433/228.1 |

FOREIGN PATENT DOCUMENTS

| | | |
|---|---|---|
| 878004 | 8/1971 | Canada. |
| 878006 | 8/1971 | Canada. |
| 987044 | 4/1976 | Canada. |
| 995667 | 8/1976 | Canada. |
| 1018294 | 9/1977 | Canada. |
| 1099848 | 4/1981 | Canada. |
| 1131827 | 9/1982 | Canada. |
| 1153391 | 9/1983 | Canada. |
| 1155141 | 10/1983 | Canada. |
| 1175196 | 9/1984 | Canada. |
| 1183144 | 2/1985 | Canada. |
| 1189996 | 7/1985 | Canada. |
| 1202749 | 4/1986 | Canada. |
| 1219990 | 3/1987 | Canada. |
| 1227202 | 9/1987 | Canada. |
| 1235423 | 4/1988 | Canada. |
| 1258465 | 8/1989 | Canada. |
| 1277070 | 11/1990 | Canada. |
| 1283663 | 4/1991 | Canada. |
| 2032556 | 6/1991 | Canada. |
| 1296015 | 2/1992 | Canada. |
| 227363 | 8/1983 | Czechoslovakia. |
| 037759 | 10/1981 | European Pat. Off.. |
| 0104491 | 4/1984 | European Pat. Off.. |
| 0188752 | 7/1986 | European Pat. Off.. |
| 2126419 | of 0000 | Germany. |
| 141667 | 5/1980 | Germany. |
| 0037759 | 10/1981 | Germany. |
| 154945 | 6/1982 | Germany. |
| 209358 | 4/1984 | Germany. |
| 214381 | 10/1984 | Germany. |
| 244748 | 4/1987 | Germany. |
| 261365 | 10/1988 | Germany. |
| 277078A1 | 3/1990 | Germany. |
| 227689 | 4/1990 | Germany. |
| 279667A1 | 6/1990 | Germany. |
| 295758 | 11/1991 | Germany. |
| 3-27308A2 | 2/1991 | Japan. |
| 52106 | 11/1937 | U.S.S.R.. |
| 311638 | 10/1971 | U.S.S.R.. |
| 311637 | 12/1971 | U.S.S.R.. |
| 349396 | 9/1972 | U.S.S.R.. |
| 545353 | 3/1977 | U.S.S.R.. |
| 549150 | 5/1977 | U.S.S.R.. |
| 1050706 | 4/1982 | U.S.S.R.. |
| 1510131 | 11/1986 | U.S.S.R.. |
| 1304987 | 4/1971 | United Kingdom. |
| 2045269 | 10/1980 | United Kingdom. |
| 2199839 | 7/1988 | United Kingdom. |
| 93/10176 | 5/1993 | WIPO. |

OTHER PUBLICATIONS

Rot et al, Chemical Abstract, vol. 89, No. 18, Oct. 30, 1978, Columbus, Ohio, US; Abstract No. 148211c; p. 71, col. 2; *abstract* & Lakokras Mater. Ikh. Primen., No. 4, pp. 50–52, 1978.

Dusek et al, Transesterification & Gelation of Polyhydroy Esters, Formed from Diepoxides & Dicarboxylic Acids, Amer. Chem. Societym 1984.

(List continued on next page.)

Primary Examiner—Thurman K. Page
Assistant Examiner—Andrew E. C. Merriam
Attorney, Agent, or Firm—Dale R. Lovercheck; James B. Bieber

[57] ABSTRACT

A root canal sealing dental filling composition, includes liquid polymerizable organic monomers and filler. The polymerizable organic monomers include an diepoxide monomer and a primary monoamine and/or a disecondary amine monomer. The filler includes 40 to 85 percent by weight of the composition and provides a radiopacity of at least 3 mm/mm Al. A method of sealing a tooth canal, includes providing a canal in a tooth sealing the canal with this root canal sealing dental filling composition.

15 Claims, No Drawings

OTHER PUBLICATIONS

Hartel et al, Zur Synthese linearer Additionspolymere aus Diandiglycidether und Dicarbonsauren, (Nov. 1984).

Klee et al, Synthesis and investigation of α, ω–methacryloyl poly (epoxide–carboxylic acid and α,ω–methacryloyl poly (epoxide–phenol)–macromonomers, Acta Polymer 44, 163–167 (1993).

Klee et al., Polym Bull. 27 (1992); 511–517.

J. Klee et al., Acta Polym. 42 (1991) 17–20.

Chemistry Abstract 115 (1991) 78952z.

Chemistry Abstract 115 (1991) 78973g.

DENTAL FILLING COMPOSITION AND METHOD

The invention relates to dental filling composition. A dental filling composition in accordance with the invention is adapted to form epoxide-amine addition polymers with fillers. The dental filling composition include filler and diepoxides, primary monoamines and/or disecondary diamines. Dental filling compositions in accordance with the invention polymerize to form a thermoplastic linear polymer which is adapted to seal a canal in a tooth root. The filler is present in an amount of from 40 to 85 percent by weight of the dental filling composition. The dental filling material is formed by polymerization and has radiopacity of greater than 3 mm/mm Al. The clinical working time is up to about 2 hours and the setting time is from about 0.5 to about 40 hours.

Blahman et al in USSR 311637 and 311638 disclose dental filling materials. Feichtinger et al in U.S. Pat. No. 3,317,469 discloses reaction product of a glycidyl polyether and diaminomethyltricyclodecane. Lee in U. S. Pat. No. 3,327,016 discloses epoxide compositions cured with 1,4-bis (aminomethyl) cyclohexane. Toepel et al in U.S. Pat. No. 3,673,558 discloses polyaddition products and process for their manufacture. Rogier in U.S. Pat. No. 4,229,376 discloses polycyclic polyamines. Rogier in U.S. Pat. No. 4,296,004 discloses polycyclic polyamines. Hörhold et al in U.S. Pat. No. 4,308,085 discloses process for the preparation of high molecular thermoplastic epoxide-amine-polyadducts. Fujisawa et al in U.S. Pat. No. 4,931,096 discloses sealer for filling a dental root canal. Chang et al in U.S. Pat. No. 4,950,697 discloses thermoplastic and injectable endodontic filling compositions. In U.S. Pat. No. 5,236,362 a root canal filling and adhesive composition is described. Polyfunctional aliphatic and aromatic amines such as hexamethylenediamine, di-ethylene triamine, triethylene tetramine, methylene dianiline or m-phenylenediamine used for the epoxide-amine polymerisation as well as tertiary amine initiators such as 2,4,6-tris(dimethylaminoethyl) phenol or triethanol amine lead to insoluble cross linked network polymers. Cross linked polymers generally tends to higher shrinkage during polymerization which gives rice to the formation of edge cracks and gaps.

Prior art dental filling materials for tooth root canals have relatively long setting time, high viscosity and discolor. Paraformaldehyde is sometimes used, as see Soviet Union Patent 1510131, and Chemical Abstracts 115 (1991) 78952z. Other products contain low molecular weight organic substances like $CHI_3$, as see Japanese Patent 9127308 A2, and Chemical Abstract 115 (1991) 78973g. Aliphatic and cycloaliphatic epoxides have been applied in dental filling materials hardened with imidazoline or $BF_3$ as see Soviet Union Patents 549150, 545353, 52106 and 349396, but are known to have mutagenic properties. Other dental filling materials contain epoxides, diethylenediamine and fillers like porcelain powder, quartz and zeolite, as see Soviet Union Patents 311638 and 311637. These fillers do not provide substantial radiopacity. The use of a setting aliphatic amine alone is disadvantageous because it does not withstand tensions caused by shrinkage and change of temperature. Aliphatic amines cause side reactions (etherification of hydroxyl groups) in epoxide-amine addition polymerization. Consequently a portion of amine groups are unreacted.

High molecular weight linear epoxide-amine addition polymers ($M_n$ 10000 to 20000 g/mol) have-been synthesised using diglycidyl ethers of bisphenols and N,N'-dibenzyldiamines, as see DD 141667, U.S. Pat. No. 4,308, 085, GB 2045269, CS 227363; or primary monoamines as see DD 154945, DD 214381, DD 261365. The addition polymers were prepared as adhesives for optical and electophotographic application.

It is an object of the invention to provide a dental filling material which provides a radiopacity of at least 3 mm/mm Al.

It is an object of the invention to provide a tooth root filling composition which has a radiopacity of at least 3 mm/mm Al and a viscosity less than 20,000 cp.

BRIEF DESCRIPTION OF THE INVENTION

A root canal sealing dental filling composition, includes liquid polymerizable organic monomers and filler. The polymerizable organic monomers include a diepoxide and a primary monoamine and/or a disecondary diamine. The filler includes 40 to 85 percent by weight of the composition and provides a radiopacity of at least 3 mm/mm Al. A method of sealing a tooth canal, includes providing a canal in a tooth sealing the canal with this root canal sealing dental filling composition.

DETAILED DESCRIPTION OF THE INVENTION

Dental filling material in accordance with the invention includes liquid polymerizable organic monomers and fillers, and is adapted for sealing tooth root canal such as are formed by root canal procedures. The polymerizable organic monomers are diepoxides, primary monoamines and/or disecondary diamines. Unsubstituted aliphatic primary monoamines, which form with diepoxide, crosslinked polymer, are not preferred as polymerizable organic monomers in dental filling material in accordance with the invention. Filler content in dental filling material in accordance with the invention is preferably from 40 to 85 percent by weight of the dental filling material as inorganic and/or organic filler particles.

A dental filling material of the invention polymerizes to form epoxide-amine addition polymers within one or more of the general formulas I, II and III as follows:

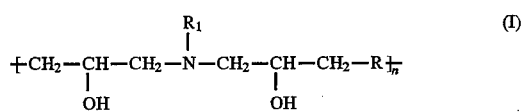

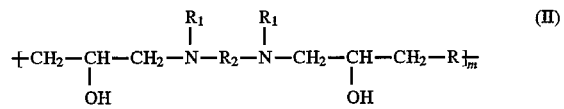

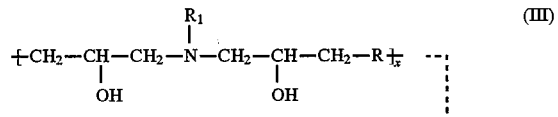

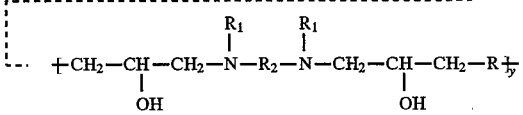

wherein R is a moiety formed from a diepoxide;

$R_1$ is a substituted alkyl, having from 2 to 12 carbon atoms, cycloalkyl, substituted cycloalkyl, aryl having from 6 to 20 carbon atoms, substituted aryl, arylalkyl, or substituted arylalkyl, $R_2$ is a difunctional alkyl, substituted alkyl having from 2 to 12 carbon atoms, cycloalkyl, substituted cycloalkyl,

3 aryl having from 6 to 20 carbonatoms, arylalkyl, substituted aryl, substituted arylalkyl, and n, m, x and y each independently is an integer from 1 to 1,000. When substituted, $R_1$ and $R_2$ are independently substituted with one or more alkoxy, halogen, nitrate, acyl or carboxy alkyl moieties.

Diepoxides useful in dental filling compositions in accordance with the invention include diglycidyl ether of bisphenol-A (2,2-Bis[4-)2,3-epoxypropoxy)phenyl] propane), diglycidyl ether of bisphenol-F (is an isomeric mixture of Bis[4-(2,3-espoxypropoxy) phenyl]methane and the 2,4-homologous (CIBA-Geigy)), butanediol diglycidyl ether, N,N-diglycidylaniline, and $\Delta^3$-tetrahydrophthalic acid (sometimes referred to as bis(2,3-epoxypropoxy) cyclohex-3-ene dicarboxylic ester). Monoamines useful in accordance with the invention are aniline, p-flouraniline, benzylamine, 1-aminoadamantan, α-phenethylamine, dimethyl (aminomethyl) phosphine oxide and ethanolamine. Diamines useful in accordance with the invention are N,N'-dibenzylethylenediamine; N,N'-dibenzyl-3,6-dioxa-octandiamine-1,8; N,N'-dibenzyl-5-oxanonandiamine-1,9; N,N'-dibenzyl-(2,2,4) trimethylhexamethylendiamine, N,N'-benzyl-(2,4,4) trimethylhexamethylendiamine.

Fillers useful in accordance with the invention are inorganic fillers including inorganic compounds, such as $La_2O_3$, $ZrO_2$, $BiPO_4$, $CaWO_4$, $BaWO_4$, $SrF_2$ and $Bi_2O_3$; organic fillers, such as polymer granulate; and combinations of organic and inorganic fillers.

Dental filling material in accordance with the invention overcomes the problems of prior art filling material, such as, discoloration and release of formaldehyde. Dental filling material in accordance with the invention provides the advantages of a low viscosity, relatively short setting time, relatively high solubility in organic solvents, thermoplastic behavior, and high radiopacity (RO) i.e., greater than 3 mm/mm Al. Higher values of the radiopacity, for example radiopacity greater than 7, mm/mm Al are obtained using as fillers $La_2O_3$, $BiPO_4$ $CaWO_4$ and $BaWO_4$.

For example a dental filling composition containing diglycidyl ether of bisphenol-A, N,N'-dibenzylethylendiamine and $CaWO_4$ show a viscosity (Brookfield) (η) of 2100 cP, a setting time of 3 hours and a radio-opacity (RO) of 9.2 mm/mmAl.

The invention provides dental filling material which is prepared from a two component paste system which is preferably introduced into roots using a lentulo or tubular needle because of the low viscosity. The dental filling material of the invention is formed with low shrinkage. This prevents contraction gaps and subsequent edge cracks of high shrinking materials. The dental filling material of the invention has low absorption of water and good adhesion to dentin. The composites formed therefrom are readily removable by heating, drilling or solublizing in organic solvents and are therefor useful as temporary filling materials.

The composition of the invention preferably has a viscosity of less than 20,000 centipoise and is preferably passed through a 1 mm diameter canal of a needle into a tooth root. The polymerizable epoxide monomer used in the composition of the invention preferably is a diglycidyl ether of bisphenol-A, digylcidyl ether of bisphenol-F, butanediol diglycidyl ether or $\Delta^3$-tetrahydrophthalic acid diglycidyl ester.

In Examples 1–4 setting times stated are determined in accordance with the method of ISO 6876 (1986-12-01: Dental root canal sealing materials).

4

EXAMPLE 1

A dental filling material is obtained by mixing homogeneously 3.404 g (10.00 mmol) diglycidyl ether of bisphenol-A, (also referred to as 2,2 bis[4-(2,3-epoxypropoxy) phenyl] propane), 2.404 g (10.00 mmol) N,N'-dibenzylethylenediamine and 18,000 g $CaWO_4$. This dental material has a viscosity (Brookfield) (η) of 3200 centipoise a setting time of 24 hours (at 37° C.) and a radiopacity of 9.5 mm/mm Al. After the polymerization the dental filling product obtained is soluble in organic solvents such as $CHCl_3$ or $CHCl_3$/ethanol-mixtures.

EXAMPLE 2

Usable thermal setting dental filling composition is prepared as a two component paste system of part A and B.

Part A is obtained by mixing homogeneously 142,570 g (374.36 mmol) diglycidyl ether of bisphenol-A (also referred to as 2,2 bis[4-(2,3-epoxypropoxy) phenyl] propane), having a number average molecular weight ($M_n$) of about 380 g/mol, 11.680 g (37.44 mmol) diglycidyl ether of bisphenol-F (which is an isomeric mixture of bis[4-(2,3-epoxypropoxy)phenyl]methane and bis[2-(2,3-epoxypropoxy) phenyl] methane sold by CIBA-Geigy), and 241.463 g $CaWO_4$, 4, 60.366 g $ZrO_2$, 0.637 g $Fe_2O_3$ and 4.277 g aerosil 200 (sold by Degussa).

The paste B is prepared by mixing homogeneously 22.064 g (205.90 mmol) benzylamine, 70.112 g (205.90 mmol) N,N'-dibenzyl-5-oxanonanediamine-1,9, 392.068 g $CaWO_4$, 98.017 g $ZrO_2$ and 25.663 g Aerosil (sold by Degussa). The volume ratio of A mixed with B is 1:1. The setting time is 7 hours (at 37° C.) and the working time 2: 23 hours (at 23° C.) , respectively. The composition is characterised by the following values: radio-opacity (RO) of 11.6 mm/mm Al, flow 45 mm, film thickness 10 µm, solubility 0.23% (all according ISO 6876), and shrinkage 1.63 volume percent.

EXAMPLE 3

Useable thermal setting dental filling composition is prepared as a two component paste system of part A and B.

Part A is obtained by mixing homogeneously 128.313 g (337.67 mmol) diglycidyl ether of bisphenol-A (also referred to as 2,2 bis[4-(2,3-epoxypropoxy) phenyl] propane) having a number average molecular weight ($M_n$) of about 380 g/mol, 10.535 g (33.77 mmol) diglycidyl ether of bisphenol-F (which is an isomeric mixture of bis[4-(2,3-epoxypropoxy) phenyl] methane, and bis[2-(2,3-epoxypropoxy) phenyl] methane sold by CIBA-Geigy), and 294.551 g $CaWO_4$, 73.638 g $ZrO_2$ 0.637 g $Fe_2O_3$ and 1.426 g Aerosil 200.

The paste B is prepared by mixing homogeneously 28.140 g (185.72 mmol) 1-amino-adamantante, 63.241 g (185.72 mmol) N,N'-dibenzyl-5-oxanonanediamine-1,9,8,544 g Aerosil 200, 365.519 g $CaWO_4$, 91.380 g $ZrO_2$ and 11.364 g OL-31 (is a silicon oil sold by Bayer). The volume ratio of A mixed with B is 1:1. The setting time is 8 hours (at 37° C.) and the working time is 16 hours at (23° C.), respectively. The composition is characterised by following values: radio-opacity (RO) of 10.1 mm.mm Al, flow 35 mm, film thickness 15 µm, solubility 0.27% (all according ISO 6876), and shrinkage 1.13 volume percent.

EXAMPLE 4

A usable thermal setting dental filling material is obtained by mixing homogeneously 2.000 g (5.88 mmool) diglycidyl ether of hisphenol-A, 1,413 g (5.88 mmol) N,N'- dibenzylethylendiamine and 8.000 g $La_2O_3$. The setting time is 6 hours (at 37° C.) and the radio-opacity is 6.3 mm/mm Al.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A root canal sealing dental filling composition, comprising: filler and liquid polymerizable organic monomers polymerized in a dental tooth root canal to form a thermoplastic linear polymer, said filler comprising 40 to 85 percent by weight of said composition and providing a radiopacity of at least 3 mm/mm aluminum, said monomers polymerize to seal said tooth root canal, and said polymerizable organic monomers being diepoxides and disecondary diamines, and said thermoplastic linear polymer is readily soluble in organic solvents, said polymerizable diepoxide monomer being diglycidyl ether of bisphenol-A, diglycidyl ether of bisphenol-F, butanediol diglycidyl ether or $\Delta^3$-tetrahydrophthalic acid diglycidyl ester.

2. A root canal sealing dental filling composition, comprising: filler and liquid polymerizable organic monomers polmerized in a dental tooth root canal to form a thermoplastic linear polymer, said polymerizable organic monomers comprising polymerizable diepoxide monomer and amine monomer, said amine monomer being a primary monamine and/or a disecondary diamine, said filler comprising 40 to 85 percent by weight of said composition and providing a radiopacity of at least 3 mm/mm aluminum, said filler being $La_2O_3$, $ZrO_2$, $BiPO_4$, $BaWO_4$, $SrF_2$, $Bi_2O_3$ and/or polymer granules.

3. A root canal sealing dental filling composition, comprising; filler and liquid polymerizable organic monomers polymerized in a dental tooth root canal to form a thermoplastic linear polymer, said polymerizable organic monomers comprising polymerizable diepoxide monomer and amine monomer, said amine monomer being a primary monamine and/or a disecondary diamine, said filler comprising 40 to 85 percent by weight of said composition and providing a radiopacity of at least 3 mm/mm aluminum, said composition being formed from two-components which are adapted to be mixed together to initiate polymerization.

4. A root canal sealing dental filling compositions, comprising: filler and liquid polymerizable organic monomers polymerized in a dental tooth root canal to form a thermoplastic linear polymer; said polymerizable organic monomers comprising polymerizable diepoxide monomer and amine monomer said amine monomer being a primary monoamine and/or a disecondary diamine, said filler comprising 40 to 85 percent by weight of said composition and providing a radiopacity of at least 3 mm/mm aluminum, said monomers being polymerized to form said thermoplastic linear polymer being within the scope of general formula:

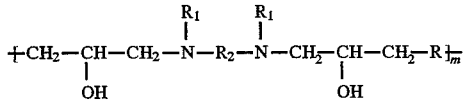

wherein R is a moiety formed from a diepoxide;

$R_1$ is a substituted alkyl, having from 2 to 12 carbon atoms, cycloalkyl, substituted cycloalkyl, aryl having from 6 to 20 carbon atoms, substituted aryl, arylalkyl, or substituted arylalkyl, $R_2$ is a difunctional alkyl, substituted alkyl having from 2 to 12 carbon atoms, cycloalkyl, substituted cycloalkyl, aryl having from 6 to 20 carbon atoms, substituted aryl, arylalkyl, or substituted arylalkyl, and m, each independently is an integer from 1 to 1,000, and when substituted, $R_1$ and $R_2$ are independently substituted with one or more alkoxy, halogen, nitrate, acyl or carboxy alkyl moieties.

5. A root canal sealing dental filling composition, comprising: filler and liquid polymerizable organic monomers polymerized in a dental tooth root canal to form a thermoplastic linear polymer, said polymerizable organic momomers comprising polymerizable diepoxide monomer and amine monomer said amine monomer being a primary monoamine and/or a disecondary diamine, said filler comprising 40 to 85 percent by weight of said composition and providing a radiopacity of at least 3 mm/mm aluminum, said monomers being polymerized to form said thermoplastic linear polymer being within the scope of general formula:

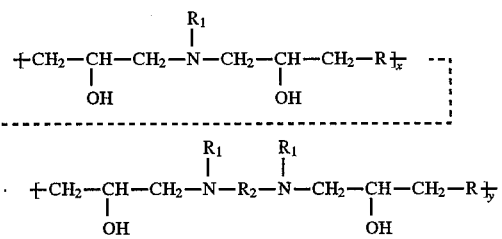

wherein R is a moiety formed from a diepoxide;

$R_1$ is a substituted alkyl, having from 2 to 12 carbon atoms, cycloalkyl, substituted cycloalkyl, aryl having from 6 to 20 carbon atoms, substituted aryl, arylalkyl, or substituted arylalkyl, $R_2$ is a difunctional alkyl, substituted alkyl having from 2 to 12 carbon atoms, cycloalkyl, substituted cycloalkyl, aryl having from 6 to 20 carbon atoms, substituted aryl, arylalkyl, or substituted arylalkyl, and x and y each independently is an integer from 1 to 1,000, and when substituted, $R_1$ and $R_2$ are independently substituted with one or more alkoxy, halogen, nitrate, acyl or carboxy alkyl moieties.

6. The composition of claim 2, 3, 4, or 5 wherein said monomers polymerize to seal said tooth root canal, and said polymerizable organic monomers are diepoxides and diamines, and said thermoplastic linear polymer is readily soluble in organic solvents.

7. The dental filling composition of claim 2, 3, 4 or 5 wherein said amine is benzylamine, adamantanamine or α-phenethylamine; and said diamine is N,N'-dibenzylethylenediamine; N,N'dibenzyl-3, 6-dioxaoctandiamine-1,8; N,N'-dibenzyl-5-oxanonandiamine-1,9; N,N'-dibenzyl-(2,2,4)-trimethylhexamethylendiamine or N,N'-dibenzyl-(2,4,4)-trimethylhexamethylendiamine.

8. The dental filling composition of claim 1, 2, 3, 4 or 5 wherein said polymer is soluble in $CHCl_3$, and/or $C_2H_5OH$.

9. The dental filling composition of claim 1, 2, 3, 4 or 5 wherein said filler provides a radiopacity of at least 6 mm/mm aluminum.

10. The dental filling composition of claim 1, 2, 3, 4 or 5 wherein said filler provides a radiopacity of at least 5 mm/mm Al.

11. The dental filling composition of claim 1, 2, 3, 4 or 5 wherein said composition is adapted to set at 37° C. within from 0.5 to 40 hours.

12. The dental filling composition of claim 1, 2, 3, 4 or 5 wherein said composition is adapted to set within from 0.5 to 3 hours.

13. The dental filling composition of claim 1, 2, 3, 4 or 5 wherein said composition has a viscosity of less than 5000 centipoise.

14. The dental filling composition of claim 1, 2 or 3, wherein said polymer is within the scope of at least one of general formulas:

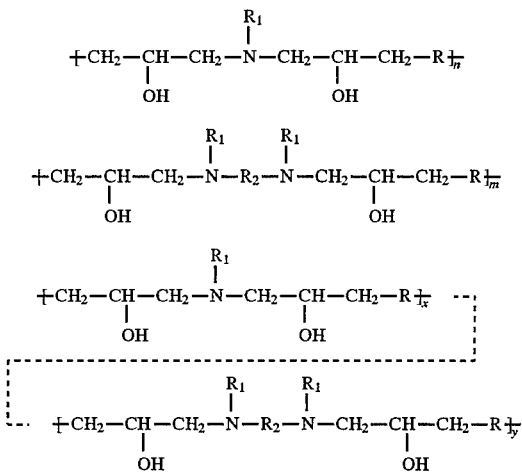

wherein R is a moiety formed from a diepoxide;

$R_1$ is a substituted alkyl, having from 2 to 12 carbon atoms, cycloalkyl, substituted cycloalkyl, aryl having from 6 to 20 carbon atoms, substituted aryl, arylalkyl, or substituted arylalkyl, $R_2$ is a difunctional alkyl, substituted alkyl having from 2 to 12 carbon atoms, cycloalkyl, substituted cycloalkyl, aryl having from 6 to 20 carbon atoms, substituted aryl, arylalkyl, or substituted arylalkyl, and n, m, x and y each index end entity is an integer from 1 to 1,000, and when substituted, $R_1$ and $R_2$ are independently substituted with one or more alkoxy, halogen, nitrate, acyl or carboxy alkyl moieties.

15. The composition of claim 1, 2 or 3, wherein said polymer is within the scope of general formula:

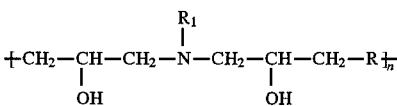

wherein R is a moiety formed from a diepoxide;

$R_1$ is a substituted alkyl, having from 2 to 12 carbon atoms, cycloalkyl, substituted cycloalkyl, aryl having from 6 to 20 carbon atoms, substituted aryl, arylalkyl, or substituted arylalkyl, and n, each index end independently is an integer from 1 to 1,000, and when substituted, $R_1$ is substituted with one or more alkoxy, halogen, nitrate, acyl or carboxy alkyl moieties.

* * * * *